US011950687B2

(12) United States Patent
Kosecoff

(10) Patent No.: US 11,950,687 B2
(45) Date of Patent: Apr. 9, 2024

(54) PORTABLE HAIR STYLING DEVICE WITH LIGHT-EMITTING DIODES EMBEDDED IN THE BRISTLES OR TEETH

(71) Applicant: L'Oreal, Paris (FR)

(72) Inventor: David B. Kosecoff, San Francisco, CA (US)

(73) Assignee: L'Oreal, Paris (FR)

( * ) Notice: Subject to any disclaimer, the term of this patent is extended or adjusted under 35 U.S.C. 154(b) by 800 days.

(21) Appl. No.: 17/035,026

(22) Filed: Sep. 28, 2020

(65) Prior Publication Data

US 2022/0095782 A1 Mar. 31, 2022

(51) Int. Cl.
*A46B 15/00* (2006.01)
*A45D 24/22* (2006.01)
(Continued)

(52) U.S. Cl.
CPC .......... *A46B 15/0036* (2013.01); *A45D 24/22* (2013.01); *A46B 5/0054* (2013.01); *A46B 11/0006* (2013.01); *A46B 11/002* (2013.01); *A46B 11/0062* (2013.01); *A46B 11/0065* (2013.01); *A46B 11/0072* (2013.01);
(Continued)

(58) Field of Classification Search
CPC ...... A46B 2200/102; A46B 2200/1033; A46B 2200/104; A46B 2200/1046; A46B 15/0036; A46B 15/0034; A46B 11/0065; A46B 11/0062; A46B 11/0089; A46B 11/0096; A46B 11/0006; A46B 11/002; A46B 11/0072; A46B 5/0054; A46B 5/0058; A45D 24/22; A61M 11/005; A61M 35/003; A61N 5/0616; A61N 5/0617; A61N 2005/0661; A61N 2005/0659; A61N 2005/0662; A61N 2005/0663;
(Continued)

(56) References Cited

U.S. PATENT DOCUMENTS 2,074,481 A 4/1937 Macmullen et al.
2004/0193235 A1 9/2004 Altshuler et al.
(Continued)

FOREIGN PATENT DOCUMENTS

EP 1666016 A1 6/2006
EP 2349477 B1 7/2012
(Continued)

OTHER PUBLICATIONS

International Search Report and Written Opinion dated Nov. 22, 2021, issued in corresponding International Application No. PCT/US2021/048413, filed Aug. 31, 2021, 28 pages.
(Continued)

*Primary Examiner* — Joseph D. Boecker
*Assistant Examiner* — Brian T Khong
(74) *Attorney, Agent, or Firm* — Christensen O'Connor Johnson Kindness PLLC

(57) ABSTRACT

A hair and scalp treatment device includes a dispenser connected to a cartridge, wherein the cartridge comprises a formulation; a plurality of tips on the device, wherein the tips have at least one opening to dispense the formulation and at least one LED that emits light in the visible color spectrum, wherein the at least one LED is located at the end of the tips; and a controller configured to individually turn on and off the LEDs from the plurality of tips.

12 Claims, 12 Drawing Sheets

(51) Int. Cl.
*A46B 5/00* (2006.01)
*A46B 11/00* (2006.01)
*A61M 11/00* (2006.01)
*A61M 35/00* (2006.01)
*A61N 5/06* (2006.01)

(52) U.S. Cl.
CPC ......... *A61M 11/005* (2013.01); *A61N 5/0616* (2013.01); *A61M 35/003* (2013.01)

(58) Field of Classification Search
CPC .... A61N 2005/0651; A61N 2005/0652; A61N 2005/0644; A61H 7/002–005
See application file for complete search history.

(56) References Cited

U.S. PATENT DOCUMENTS

| | | | |
|---|---|---|---|
| 2007/0154863 A1* | 7/2007 | Cai | A46B 11/0062 433/89 |
| 2008/0140164 A1* | 6/2008 | Oberreiter | A61N 5/0616 606/9 |
| 2008/0172115 A1* | 7/2008 | Gourgouliatos | A61N 5/0617 607/94 |
| 2009/0025247 A1 | 1/2009 | Yde et al. | |
| 2009/0036954 A1 | 2/2009 | Ragazzi et al. | |
| 2009/0234253 A1* | 9/2009 | Vandenbelt | A46B 13/023 15/105 |
| 2011/0308034 A1 | 12/2011 | Powers et al. | |
| 2012/0123305 A1* | 5/2012 | Pearl | A45D 24/00 604/20 |
| 2019/0098974 A1* | 4/2019 | Grez | A45D 24/26 |
| 2019/0143138 A1* | 5/2019 | Segal | A61N 5/0617 607/88 |
| 2019/0344095 A1 | 11/2019 | Landa et al. | |
| 2020/0170399 A1 | 6/2020 | Truong | |
| 2020/0346030 A1* | 11/2020 | Tung | A46B 15/0059 |
| 2021/0101018 A1* | 4/2021 | Dijkstra | A61H 23/02 |

FOREIGN PATENT DOCUMENTS

| | | |
|---|---|---|
| WO | 2006/086470 A2 | 8/2006 |
| WO | 2010/045973 A1 | 4/2010 |
| WO | 2018/237346 A1 | 12/2018 |

OTHER PUBLICATIONS

International Preliminary Report on Patentability, dated Apr. 6, 2023, in corresponding International Patent Application No. PCT/US2021/048413, 11 pages.

* cited by examiner

PORTABLE HAIR STYLING DEVICE WITH LIGHT-EMITTING DIODES EMBEDDED IN THE BRISTLES OR TEETH

SUMMARY

In one embodiment, a brush or comb hair and scalp treatment device has controllable LEDs that emit light in the visible color spectrum, or a UV (ultraviolet) or IR (infrared) or both UV and IR LED embedded in bristle or teeth tips for targeted treatments and displaying of information or pleasing visuals.

In one embodiment, the device can turn on different wavelength LEDs to use for various hair and scalp treatment applications and curing and treatment of various hair and scalp formulas or serums.

In one embodiment, the scalp and hair treatment device increases the effectiveness of such treatments by placing the active light components in the region(s) of the device that make contact with or get closest to the targeted skin, scalp, or hair root regions.

In one embodiment, the ability to produce different colors from emitters arranged into rows and columns with the tips are used to display detailed device information, such as charge status, operating mode, cartridge fill level, or pleasing visuals by creating a RGB pixel-like display.

In one embodiment, electrically conductive wiring is routed through hollowed bristle tips. Alternatively, bristle tips are made up of a conductive spring-like coils. These conductive paths lead to visible color spectrum LEDs and UV and IR LEDs (light-emitting diodes) housed in the tips. The components are potted and sealed with a transparent cap. The LEDs are controlled via signals along these conductive paths. These signals are driven by a controller circuit housed in the main body of the device.

In one embodiment, the device folds into itself. When the device is in the folded configuration, the LEDs are positioned behind a diffuser, and the visuals created by the LEDs can be made more recognizable, as the visual gaps between the LEDs and tips can be filled in by the diffuser material.

In one embodiment, a brush or comb hair and scalp treatment device has controllable electromagnetic energy emitters configured to emit light in the visible color spectrum, or a UV (ultraviolet) or IR (infrared) or both UV and IR LED. Non-limiting examples of electromagnetic energy emitters include arc flashlamps, continuous wave bulbs, incandescent emitters, laser diodes, light-emitting diodes (e.g., high-efficiency UV light-emitting diodes, microcavity light-emitting diodes, organic light-emitting diodes, polymer light-emitting diodes, polymer phosphorescent light-emitting diodes or the like), optical energy emitters, quantum dots, or the like.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Individuals are washing hair with traditional wet water-based shampoo less and less frequently. A number of reasons can be offered for the reduction in this type of shampoo, such as preventing hair-loss and hair damage or saving time and energy. Dry shampoos are on the rise. People are trying to prolong time in-between salon visits to save money, leading to growing interest in tinted dry shampoos for root touch-up. Dry shampoos are primarily packaged in spray bottles. However, spray bottles create concerns about inhaling the product and unintentional spraying of the face, particularly the eyes. Spray bottles are imprecise in both spray direction and spray amount. Further, spray bottles are not appropriate when traveling or using public bathrooms. Dry shampoos do not clean the scalp and in fact can damage it. Nevertheless, there is a belief that caring for the scalp leads to healthy hair. 'Dry' methods of cleaning the scalp involve either brushing or preening to spread the oils onto hair. Scalp treatment and scalp-directed formulas can be applied via pipettes, foams or powders, and require manually parting your hair. Powders and foams get on hands. Dripping excessive product onto scalp can create runoff and greasy-looking hair. Reusable and closed-loop product design is a growing demand.

Disclosed is a brush or comb hair and scalp treatment device with controllable electromagnetic energy emitters configured to emit light in the visible color spectrum, or a UV (ultraviolet) or IR (infrared) or both UV and IR LED. Non-limiting examples of electromagnetic energy emitters include arc flashlamps, continuous wave bulbs, incandescent emitters, laser diodes, light-emitting diodes (e.g., high-efficiency UV light-emitting diodes, microcavity light-emitting diodes, organic light-emitting diodes, polymer light-emitting diodes, polymer phosphorescent light-emitting diodes or the like), optical energy emitters, quantum dots, or the like.

Figure 1:
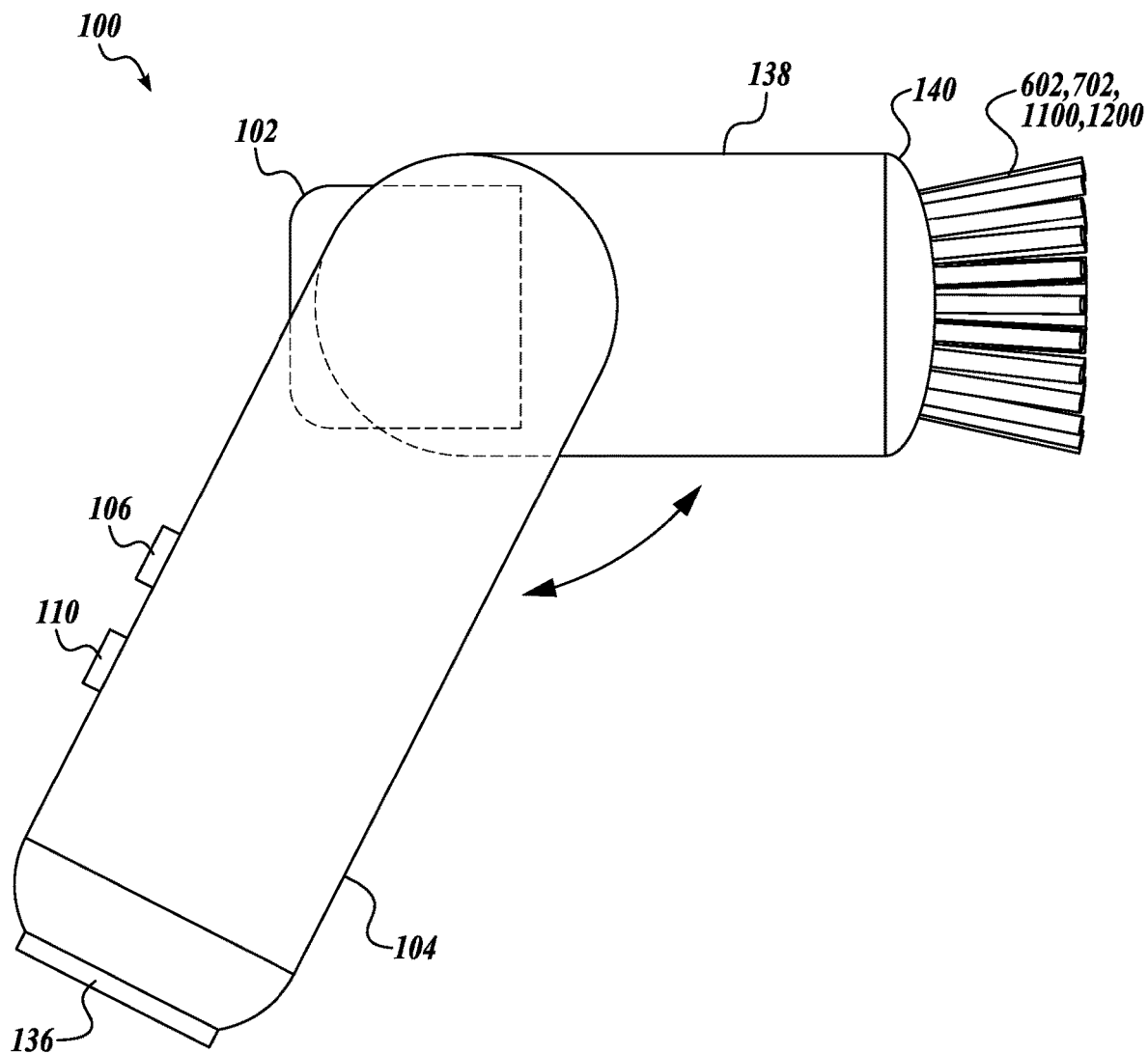
FIG. 1 is a diagrammatical illustration of a hair and scalp treatment device.
Figure 2:
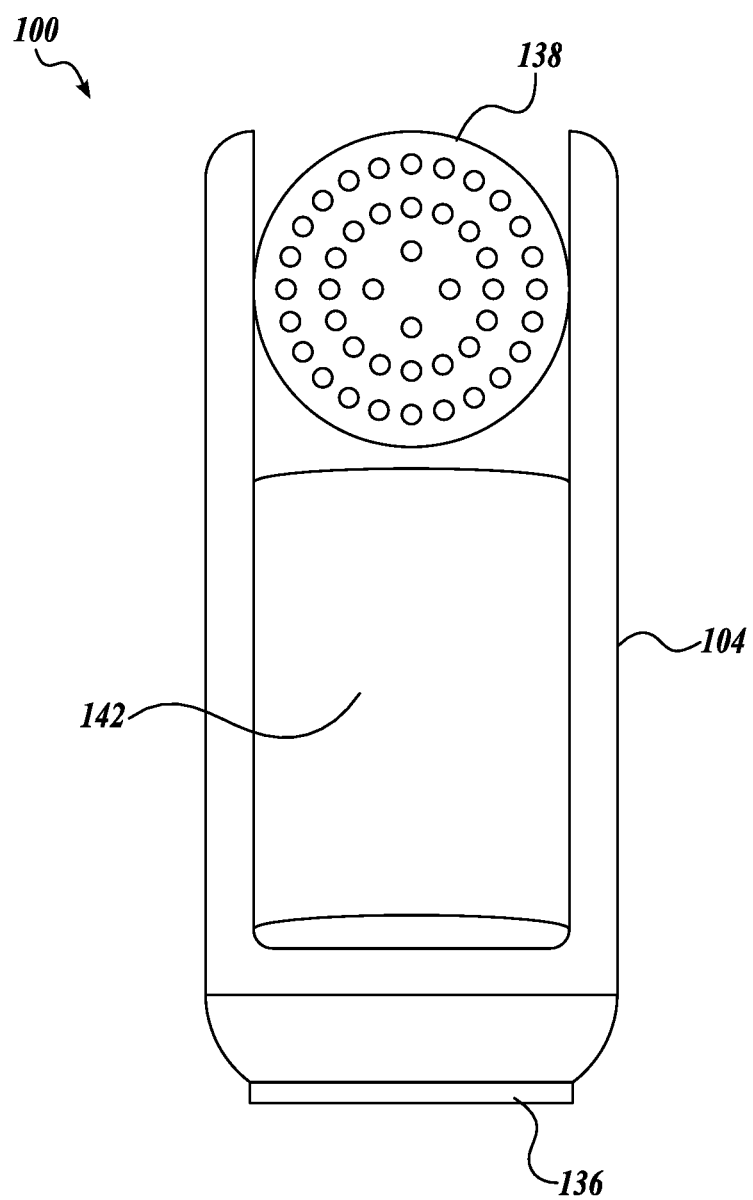
FIG. 2 is a diagrammatical illustration of the front of the hair and scalp treatment device of FIG. 1 in the open (unfolded) configuration.
Figure 3:
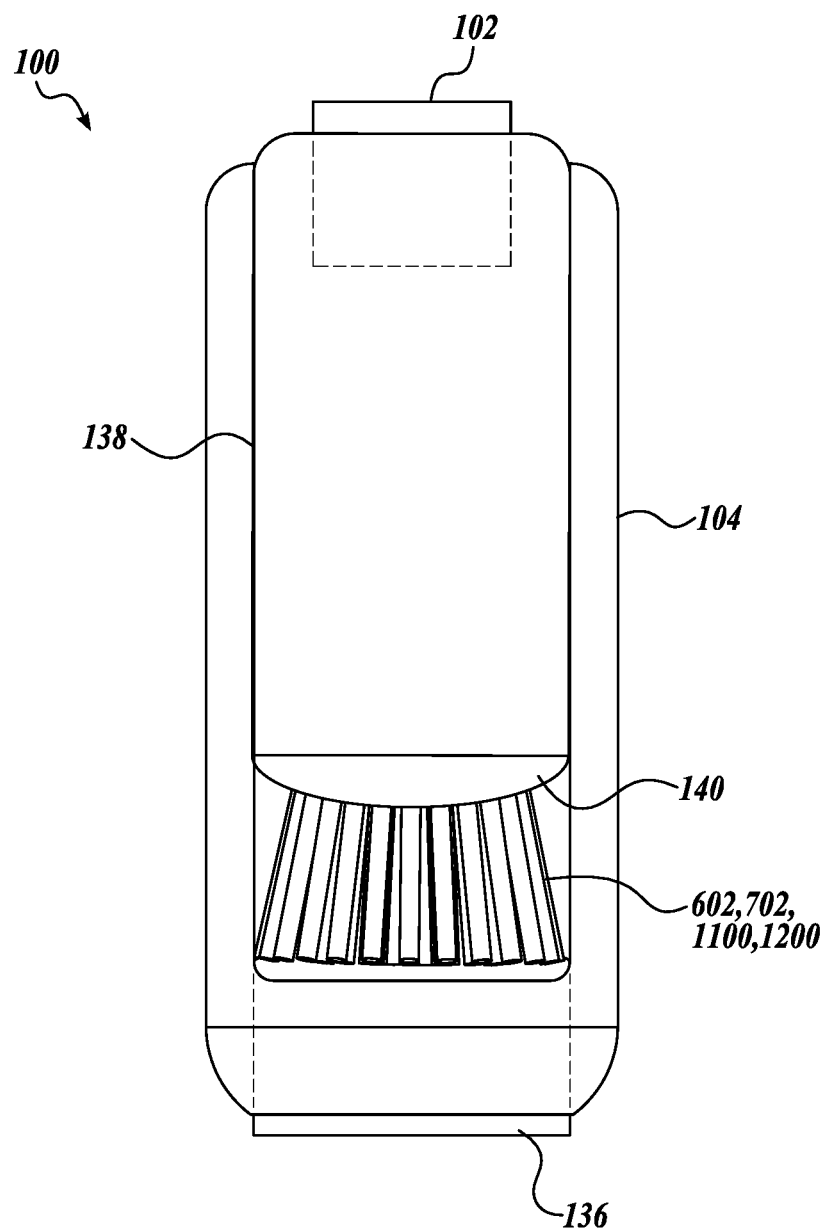
FIG. 3 is a diagrammatical illustration of the front of the hair and scalp treatment device of FIG. 1 in the closed (folded) configuration.

Referring to FIGS. 1 to 3, a hair and treatment device 100 includes controllable LEDs embedded in brush tips 602, 702, 1100, 1200 for targeted treatments and displaying of information or pleasing visuals. Although the illustrations depict a brush embodiment, the tips can be arranged into a comb embodiment, i.e., in a single row of tips.

In one embodiment, the device 100 selects to turn on LEDs of different wavelengths for various hair and scalp treatment applications and for the curing and treatment of various hair and scalp formulas or serums. The device 100 can control the rate at which the LEDs are turned on and off and the brightness and intensity of each LED at its respective wavelength.

In one embodiment, the scalp and hair treatment device 100 increases the effectiveness of such treatments by placing the active light components in the region(s) of the device 100 that make contact with or get closest to the targeted skin, scalp, or hair root regions. In one embodiment, the active light components are placed at the ends of the tips.

In one embodiment, the scalp and hair treatment device 100 uses LEDs that emit light in the visible color spectrum to create different colors at the tips. The visible color light LED emitters placed on the tips that are arranged into rows and columns are used to display detailed device information, such as charge status, operating mode, cartridge level, or pleasing visuals by creating a RGB pixel-like display. RGB (red-green-blue) LEDs are used as a representative example of LEDs that emit light in the visible color spectrum to demonstrate aspects of the disclosure, and other LEDs emitting light in the visible color spectrum can be used in place of the RGB LEDs.

In one embodiment, electrically conductive wiring is routed through hollowed bristle tips. Alternatively, bristle tips are made up of a conductive spring-like coils. These conductive paths lead to the visible light spectrum LEDs and UV and IR LEDs (light-emitting diodes) housed in the tips. The components are potted and sealed with a transparent cap. The LEDs are controlled via signals along these conductive paths. These signals are driven by a controller circuit housed in the main body of the device 100.

In one embodiment, the device 100 folds into itself. When the device 100 is in the folded configuration, the LEDs are positioned behind a diffuser, and the visuals created by the LEDs can be made more recognizable, as the visual gaps between the LEDs and tips can be filled in by the diffuser material.

Referring to FIGS. 1 to 3, in one embodiment, the device 100 includes a handle 104 connected to a substantially cylindrical section 138. The section 138 can be circular in cross section or have any other shape, such as oblong, rectangular, square, or combination of shapes. The handle 104 is connected to the device 100 at an obtuse angle with respect to the front end of the device 100. The handle 104 helps balance the device weight for more comfortable use and easier control. The control buttons can also be located on the handle.

In one embodiment, the device 100 includes a body structure that has a substantially cylindrical section 138 from the back end, where a cartridge 102 fits, to the front end having a brush head 140. In one embodiment, the handle 104 connects to the back side of cylindrical section 138.

The brush head 140 is the part of the device 100 that holds the tips 602, 702, 1100, or 1200. In one embodiment, the device 100 has the tips 602, 702, 1100, 1200 arranged in a brush configuration, such as concentric circles. In one embodiment, the tips are also configured to enable controlling the dispensing of formulations from selected individual tips and not others. This allows "turning on" some tips while leaving other tips "turned off" to create different spray patterns from the brush head 140. Similarly, for visible color spectrum and UV and IR LEDs, the LEDs at the tips are turned on and off individually, so that some tips may light up with color and other tips are not lit.

In one embodiment, the handle 104 is connected to the cylindrical section 138 via a pivoting connection. In this manner the cylindrical section 138 can fold inside the handle 104 when not in use.

In FIG. 1, the device 100 is illustrated showing the cylindrical section 138 with brush head 140 on the end in the unfolded position which renders the device operational. In FIG. 2, the device 100 is illustrated from the front showing that the device can include a cavity 142 within the handle 104. In FIG. 3, the device 100 is illustrated with the cylindrical section 138 and brush head 140 in the folded position with the cylindrical section 138 and brush head 140 receding into the handle 104 and coming to rest within the cavity 142.

In one embodiment, in the folded position, the tips 602, 702, 1100, 1200 are positioned next to a diffuser material 136. The diffuser material 136 is located at the end of the handle 104, and the diffuser material 136 has an exterior surface so as to be visible to one from the exterior, i.e., visible by looking down the end of the handle 104. The tips point in the direction of the diffuser material 136. The diffuser material 136 is fully transparent to light or is translucent or has a degree of opacity, but not fully opaque, to allow some light emitted by the tips to be visible from the exterior of the diffuser material 136. In one embodiment, the diffuser material 136 produces a softer light by scattering the emitted light to fill in the gaps between the tips.

In one embodiment, the device 100 includes a housing that accepts a removable cartridge 102 containing a hair or scalp treatment formulation. The device 100 allows cartridges 102 to be swapped readily to provide different formulations. The cartridge 102 can be configured to be a re-Tillable cartridge or a disposable cartridge. In one embodiment, the device 100 can be configured to hold more than one cartridges 102, wherein each cartridge can be filled with a different formulation for a different treatment. Alternatively, some applications may use two or more different formulations that require applying both formulations to achieve the intended treatment.

In one embodiment, the tips 602, 702, 1100, 1200 are configured to be able to dispense two different formulations. In an embodiment, the tips 602, 702, 1100, 1200 have hollow chambers that extend the entire length of the tips. Tips 602, 702, 1100, 1200 are at least one diameter in length. However, tips 602, 702, 1100, 1200 can be constructed to be several diameters in length, so the width to length ratio can vary from 1 to 1 to 1 to 20 or more. The tips 602, 702, 1100, 1200 can be flexible or non-flexible. Tips 602, 702, 1100, 1200 can also be connected on the brush head 140 in a flexible matter. The segregated chambers in the tips allow one or more formulations to be delivered through each chamber without mixing. The formulations can be segregated within the respective chambers until the time the formulations exit the chambers. The dispensing of formulations can be accomplished by constructing each of the chambers with openings along the length or only at the ends or both along the length and ends of the chambers. Further, each of the chambers in the tips can have a valve or other means to control dispensing only from one chamber or both chambers. Controlling the dispensing of formulations from only certain tips on the brush head 140 allows the creation of multiple patterns for dispensing, for example, cone spray, fan spray, and the like.

In an embodiment, chambers are depicted as half-cylinders and full cylinders, but the chambers may take on any cross-sectional shape. Additionally, in an embodiment, the tips 602, 702, 1100, 1200 and the first and second hollow chambers forming them can be electrically conductive so as to be configured as a positive and negative terminal to further provide micro-currents or to the scalp and hair. Further, conductive tips 602, 702, 1100, 1200 have other uses when the first and second hollow chambers are connected to a positive and negative terminal of a power supply or the first and second hollow chambers are connected to a positive and negative sensing terminal.

In one embodiment, the tips 602, 702, 1100, 1200 do not need to conductive, but the multi-cylinder construction can still be useful if the application involves mixing formulations or dispensing formulations and vacuuming onto a small, controlled target area on the scalp.

Figure 4:
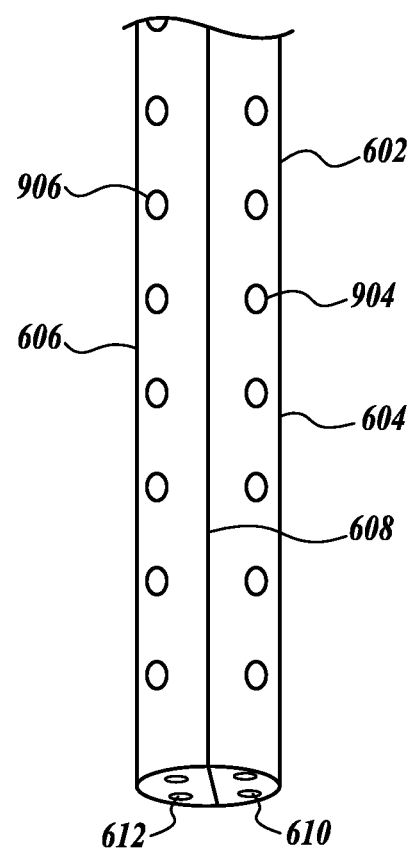
FIG. 4 is a diagrammatical illustration of a tip utilizing half cylinder construction for the brush and comb embodiments.

Referring to FIG. 4, in one embodiment, the tip 602 is constructed as joining a first hollow half cylinder 604 to a second hollow half cylinder 606 along the length direction. The first 604 and second 606 half cylinders can be made from an electrically conductive material. In one embodiment, the first 604 and second 606 half cylinders are separated by an electrical insulator 608. Here, although the overall shape of the tip 602 is of a "cylinder," according to this disclosure the tip 602 can have any cross-sectional shape, including oblong, rectangular, square, or any other polygon.

In one embodiment, the first hollow half cylinder 604 and the second 606 hollow half cylinder are made from a conductive material such as metal. In one embodiment, one of the first 604 or second 606 half cylinder can be designated a positive conductor terminal and the other half cylinder will be designated a negative conductor terminal.

In one embodiment, the first 604 and second 606 hollow chambers are made from or could be embedded with a shape memory or piezoelectric material that can be actuated by an electric current to control a direction of movement of the tips 602. In one embodiment, the chambers in a dual-chamber construction could be made of or embed a shape memory or piezoelectric materials that actuate in opposing directions from one another, allowing for plus and/or minus actuation about a center position depending on which chamber is activated. These materials can exist as polymers, ceramics, and alloys, for example. In one embodiment, the shape memory and piezoelectric materials can be fabricated as coils, and do not necessarily have to be hollow chambers. Coils can be effective for actuating the tips vertically along the Z axis (i.e., in the axial direction of the coil). Electrical actuation of the shape memory and piezoelectric materials is via an AC or DC power source having a positive and negative terminal connected to the shape memory or piezoelectric material.

FIG. 4 further illustrates that tips 602 can have openings 904 on the exterior circumference. The hollow half cylinder 604 has first openings 904 along a length of the exterior, and the hollow half cylinder 606 has second openings 906 along a length of the exterior. In one embodiment, the openings 904, 906 can be made by laser-cutting holes (perforations) along the length of tip 602.

In one embodiment, tips 602 can omit openings along the length of the tips, and the tips 602 are provided with openings only at the very ends so as to use the tips 602 for treatment of the scalp. In this way, two different formulations can be delivered from tips 602 via the half cylinder 604 and the half cylinder 606.

In one embodiment, the end of the tips 602 include a perforated flat or domed disk having small openings 610 in the first half cylinder 604 and openings 612 in the second half cylinder 606. In one embodiment, instead of a disk, the half cylinders 604 and 606 can be completely open at the end. Either construction allows dispensing formulation from the ends or along the length of the tips 602 or both along the length and ends of the tips 602.

Figure 5:
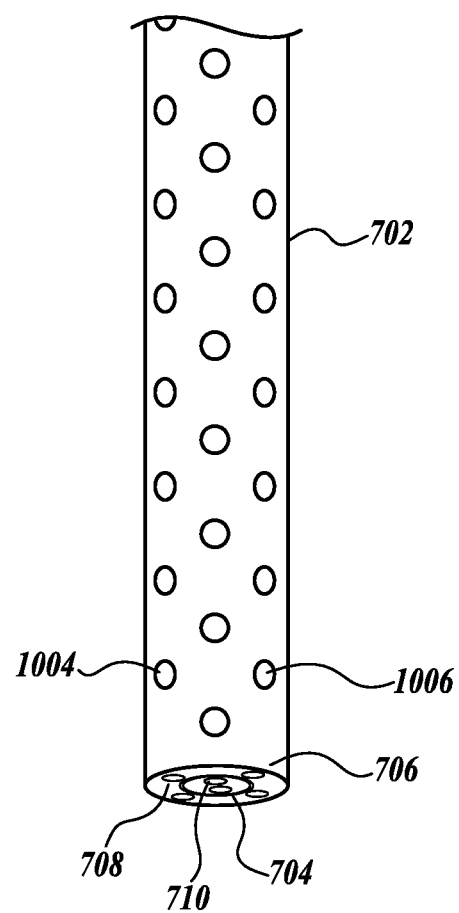
FIG. 5 is a diagrammatical illustration of a tip utilizing full cylinder within cylinder construction for the brush and comb embodiments.

Referring to FIG. 5, in one embodiment, the tip 702 is constructed by inserting a first hollow small diameter cylinder 704 into a second hollow larger diameter cylinder 706. In one embodiment, the first cylinder 704 is coaxial with the second cylinder 706. The first cylinder 704 may be called the inner cylinder and the second cylinder 706 may be called the outer cylinder. Here, although the tip 702 is in the shape of a "cylinder,", according to this disclosure a tip can have any cross-sectional shape, including oblong, rectangular, square, or any other polygon.

In one embodiment, the first cylinder 704 and the second 706 cylinder are made from a conductive material such as metal. In one embodiment, the exterior of the first smaller cylinder 704 can be coated with an insulator. An insulator is optional if the first 704 and second 706 cylinders cannot be electrically isolated from each other. In one embodiment, one of the first 704 or second 706 cylinders will be designated a positive conductor terminal and the other cylinder will be designated a negative conductor terminal.

In one embodiment, the first 704 and second 706 hollow chambers are made from or could be embedded with a shape memory or piezoelectric material that can be actuated by an electric current to control a direction of movement of the tips 702. In one embodiment, the chambers in a dual-chamber construction could be made of or embed a shape memory or piezoelectric materials that actuate in opposing directions from one another, allowing for plus and/or minus actuation about a center position depending on which chamber is activated. These materials can exist as polymers, ceramics, and alloys, for example. In one embodiment, the shape memory and piezoelectric materials can be fabricated as coils, and do not necessarily have to be hollow chambers. Coils can be effective for actuating the tips vertically along the Z axis (i.e., in the axial direction of the coil). Electrical actuation of the shape memory and piezoelectric materials is via an AC or DC power source having a positive and negative terminal connected to the shape memory or piezoelectric material.

In FIG. 5, the inner cylinder 704 has first openings 1004 that appear on the exterior of outer cylinder 706; however, openings 1004 can be connected passing through the outer cylinder 706, so that openings are closed off to the outer cylinder 706, for example, by tubes that lead to the inner cylinder 704. The outer cylinder 706 has second openings 1006 along a length of the exterior, wherein openings 1006 only connect to the interior of the outer cylinder 706. In an embodiment, the inner cylinder 704 and outer cylinder 706 are not coaxial with each other, but, the inner cylinder 704 may be placed against the inner wall of the outer cylinder 706, thus, the openings from the inner cylinder 704 may only need to traverse the wall of the outer cylinder 706, thus, avoiding the need to connect openings via tubes. An insulator may need to be interposed between the inner 704 and outer 706 cylinders for electrical isolation. In either construction, two different formulations can be delivered from tips 702 via the inner 704 and outer cylinder 706. In one embodiment, the openings 1004, 1006 can be made by laser-cutting holes (perforations) along the length of tip 702.

In one embodiment, the end of the tips 702 include a perforated flat or domed disk having small openings 710 in the first inner cylinder 704 and openings 708 in the second outer cylinder 706. In an embodiment, instead of a disk, the inner and outer cylinders 704 and 706 can be completely open at the end. Either construction allows dispensing formulation from the ends or along the length of the tips 702 or both along the length and ends of the tips.

In one embodiment, when the tips 602 and 702 are made from conductive materials, one of the cylinders 604 or 606 and 704 or 706 of each of the tips 602 and 702 may serve as a positive terminal and the other to act as a negative terminal for the conduction of electrical charges. This allows powering devices, such a LEDs or sensors.

Figure 6:
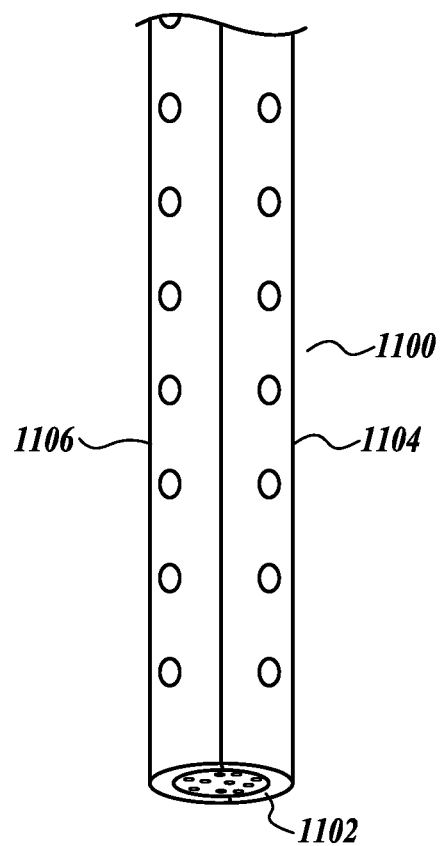
FIG. 6 is a diagrammatical illustration of a tip with LEDs of half cylinder construction for the brush and comb embodiments.

FIG. 6 illustrates a tip 1100, similar to tip 602 in construction, made from an electrically conductive first hollow half cylinder 1104 placed side-by-side, but electrically isolated, to an electrically conductive second hollow half cylinder 1106, wherein the first half cylinder 1104 is designated as a positive or negative terminal, and the second half cylinder 1106 is the terminal of opposite polarity as the first half cylinder 1104. An electrically insulating material or coating can be added between the first 1104 and second 1106 hollow half cylinders for electrical isolation. A power source is connected to the first 1104 and second 1106 half cylinders. In one embodiment, this allows placing one or more light-emitting diodes 1102 at the end of the tip or other locations that is powered by the two half cylinder serving as terminals by being in contact with the positive and negative terminals.

Figure 7:
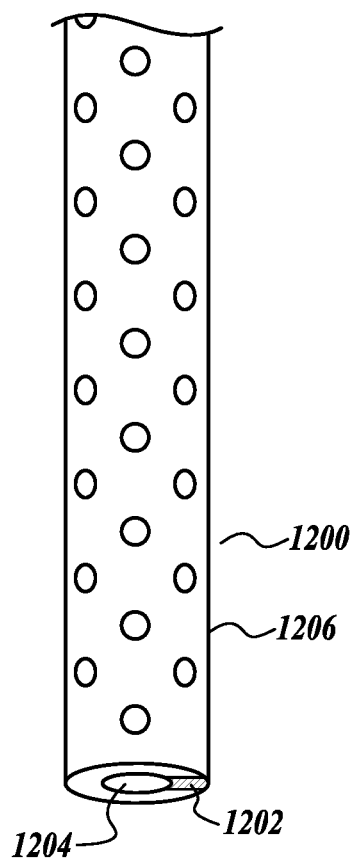
FIG. 7 is a diagrammatical illustration of a tip with LEDs of full cylinder within cylinder construction for the brush and comb embodiments.

FIG. 7 illustrates a tip 1200, similar to tip 702 in construction, made from an electrically conductive first hollow inner cylinder 1204 placed inside or coaxially within an electrically conductive second hollow outer cylinder 1206, wherein first inner cylinder 1204 is a positive or negative terminal, and the second outer cylinder 1106 is the terminal of opposite polarity to the first cylinder 1204. An electrically insulating material or coating can be added between the first 1204 and second 1206 hollow cylinders for electrical isolation. A power source is connected to the first inner 1204 and second outer 1206 cylinders. In one embodiment, this allows placing one or more light-emitting diodes 1202 at the end of the tip or other locations that is powered by the two cylinders serving as terminals by being in contact with the positive and negative terminals.

In one embodiment, depending on the power of the LEDs 1102 and 1202, thermal dissipation can be absorbed (heat-sinked) by the conductive material of the cylinders 1104, 1106, 1204, and 1206.

In one embodiment, when the LEDs 1102 and 1202 are placed at the end of the tips, the LEDs can deliver more energy to the scalp compared to being placed at the base of the tips or when the LED light is delivered through a long fiber-optic path.

In one embodiment, the LEDs 1102 and 1202 can be used for treatment, curing formula, or indicating device status (i.e., operational mode or charging status).

LEDs can be any type of a single wavelength (laser LED) or of a range of wavelengths. In one embodiment, light therapy has been used on the scalp to treat a skin condition. In one embodiment, light therapy has been used to stimulate the cells of hair follicles. The intensity of the light produced by the LEDs 1102, 1202 can be varied by controlling the current, for example.

In one embodiment, the LEDs 1102, 1202 include one or more Group III-V (GaAs) based LEDs that are capable of emitting electromagnetic radiation at wavelengths in a range spanning from green visible light to near infrared. In one embodiment, the LEDs 1102, 1202 include one or more Group III-nitride blue LED solid state emitters that are capable of emitting electromagnetic radiation at wavelengths in a range spanning from ultraviolet to blue visible light.

In one embodiment, the wavelength output of the LEDs 1102, 1202 includes one or more gallium-indium-nitrogen (GaInN) LEDs that have a wavelength output of about 360-370 nm. In other embodiments, the LEDs 1102, 1202 emit electromagnetic energy in a range of wavelengths from about 200 nm to about 2000 nm, which includes wavelengths in the ultraviolet range (about 350 nm) and near infrared (about 1200 nm).

Figure 10:
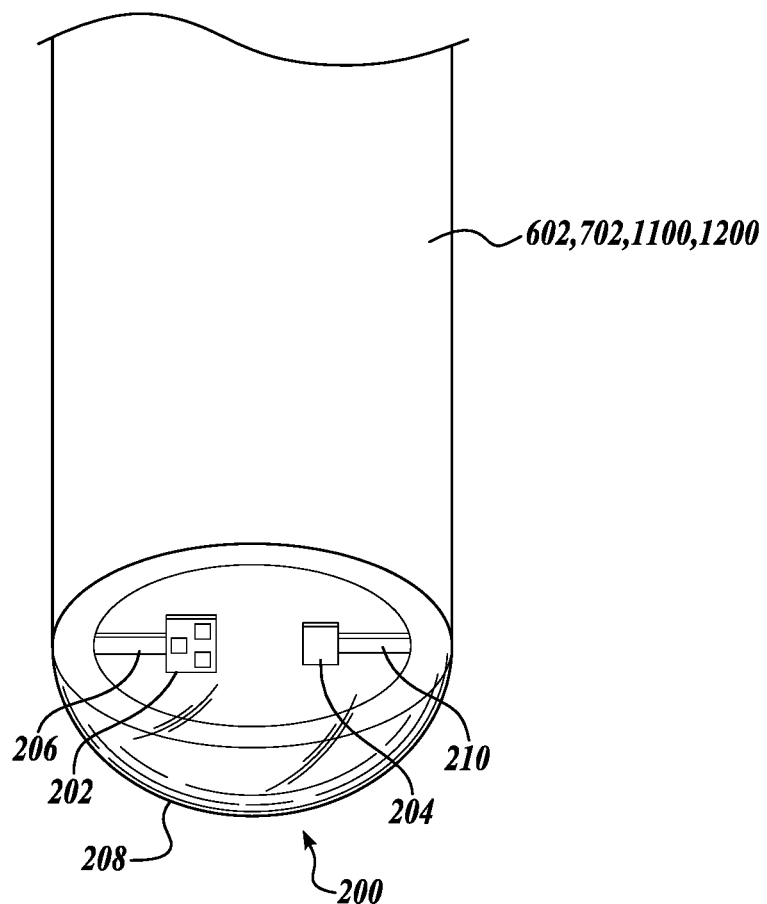
FIG. 10 is a schematic illustration showing an individual tip having at least one LED that emits light in the visible color spectrum and at least one UV or IR LED.

Referring to FIG. 10, one embodiment of an arrangement of LEDs 200 that may be used with tips 602, 702 is illustrated. When tips 602, 702 are fitted with LEDs as illustrated in FIG. 10, the tips 602, 702 may omit dispensing openings on the end. In one embodiment, the tips 602, 702, include at least one visible color spectrum LED, such as a RGB (red-green-blue) LED 202 and/or at least one UV or IR LED 204 or both UV and IR. Although RGB LEDs are used as a representative example to demonstrate aspects of the disclosure, other LEDs emitting light in the visible color spectrum can be used in place of the RGB LED 202. The visible color spectrum of the electromagnetic radiation spectrum is generally considered to be from about 380 nm (violet) to about 740 nm (red).

Figure 12:
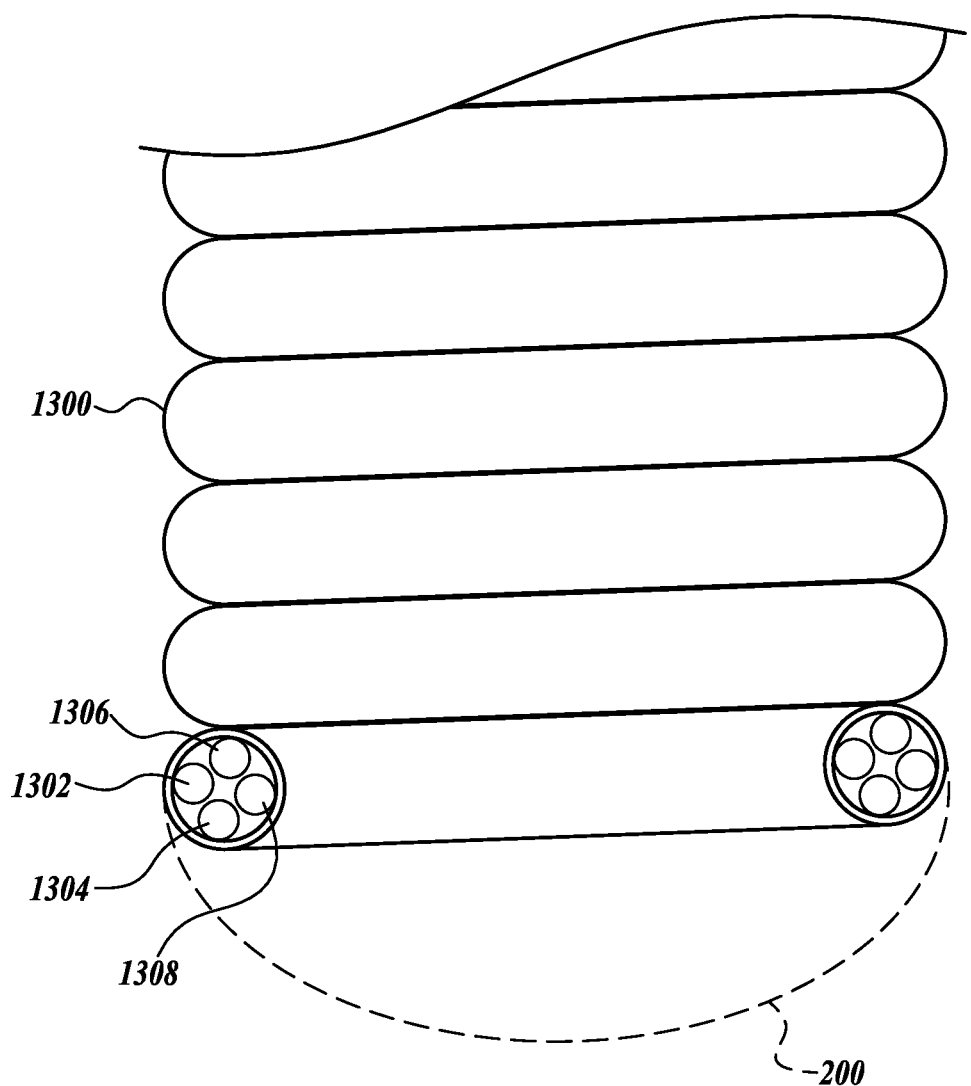
FIG. 12 is an embodiment of a tip constructed into spring-like coils with conductive wiring.

In one embodiment, RGB LEDs produce three nominal wavelengths that are chosen for maximizing the range of perceived colors by varying their intensities. An RGB LED 202 can include three LEDs, one for each color red, green, and blue, in one package. In one embodiment, red light has a wavelength of about 620 to 750 nm, green light has a wavelength of about 495 to 570 nm, and blue light has a wavelength of about 450 to 495 nm. In one embodiment, the RGB LED 202 includes wiring for a common cathode and three anodes, one for each red, green, and blue LED. In one embodiment, the RGB LED 202 includes wiring for a common anode and three cathodes. FIG. 12 is an illustration of an embodiment of a tip 1300 with the LED construction 200 at the end. The tip 1300 can be used in place of tip constructions 602 and 702. In one embodiment, the tip 1300 is constructed into spring-like coils with multiple (four) conductive wirings 1302, 1304, 1306, 1308 to control an RGB LED 202, for example. In one embodiment, the voltage to each of the red, green, and blue LEDs is independently modulated to turn on and vary the intensity of one or more of the LEDs in the RGB LED 202. The red, green, and blue LEDs are used to produce any color that is a combination of two or more colors.

In one embodiment, the RGB and UV or IR LEDs 202, 204 are potted and sealed with a light transparent cap 208, such as epoxy. The LEDs 202 and 204 are controlled via signals along conductive wiring paths 206 and 210, such as the cylinders themselves or dedicated wiring in view of the RGB LED requiring distinct signals for each of the red, green and blue LEDs. The signals to power the LEDs 202 and 204 are driven by a light controller circuit housed in the main body of the device.

Figure 8:
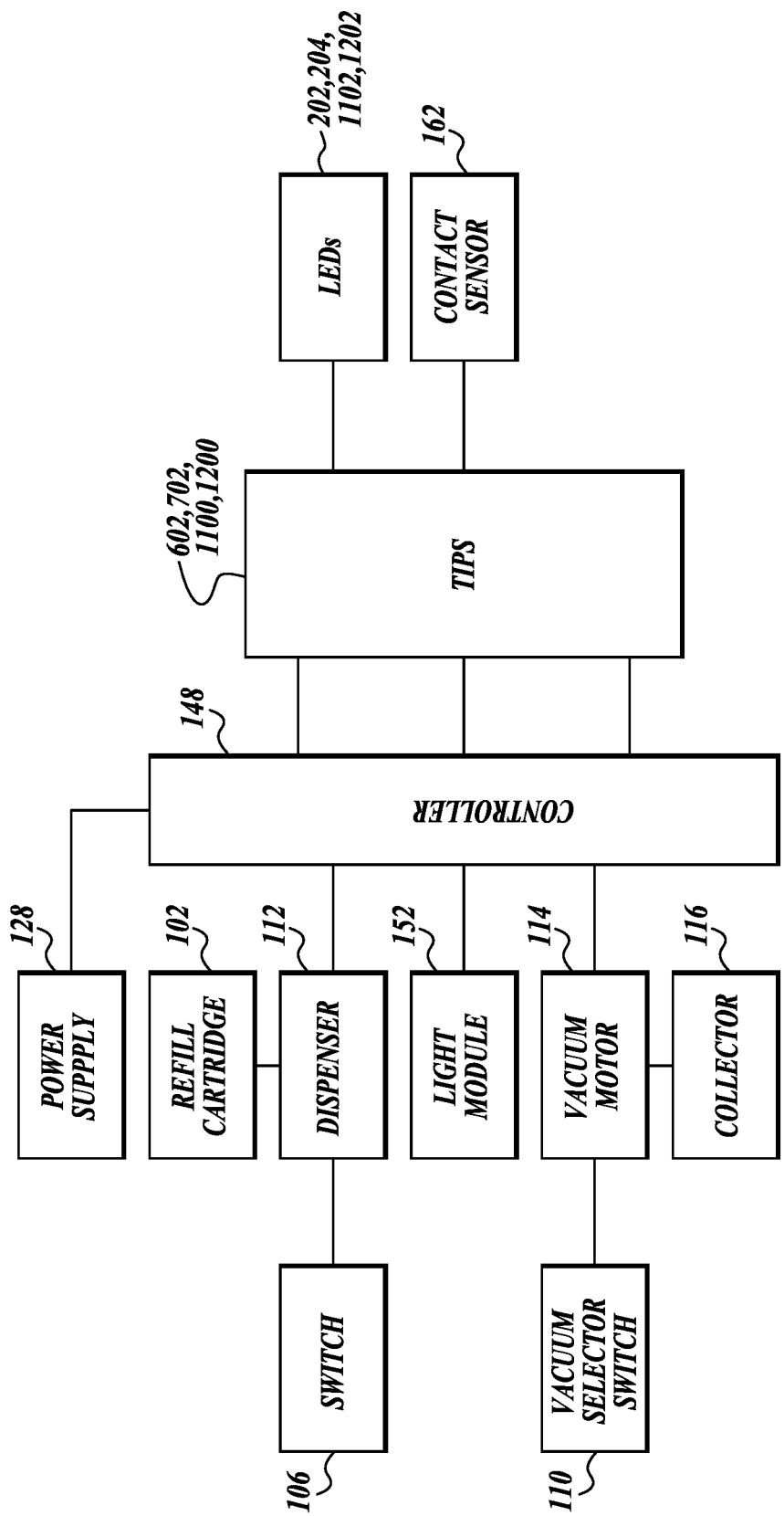
FIG. 8 is a schematic illustration showing the components of an embodiment of a hair and scalp treatment device.

Referring to FIG. 8, the device 100 is represented schematically to illustrate the main systems.

In one embodiment, the device 100 includes a power supply 128. The device 100 can be powered by alternating current (AC) or direct current (DC). In one embodiment, the device 100 is powered through common household alternating current that relies on an electrical cord (not shown) to supply power to the device 100. In one embodiment, the device 100 is powered through direct current, such as a rechargeable battery that can be charged by plugging into a household alternating current outlet. A direct current powered device 100 allows the device to be used without staying or standing in proximity to an electrical outlet. The power supply 128 is configured to provide power to any of the systems requiring power, such as a controller 148, dispenser 112, light module 152, vacuum motor 114, camera 160, LEDs 1102, 1202, and at the tips 602, 702, 1100, and 1200.

In one embodiment, the device 100 includes a formulation dispenser 112. In one embodiment, the formulation is stored in the replaceable or refillable cartridge 102. Cartridges 102 can be removable from the device 100 either to be re-filled or for disposal and replacement with a new full cartridge. Once emptied, a cartridge 102 can be replaced with a new cartridge filled with the same or different formulation or the cartridge can be refilled with the same or different formulation. As seen in FIG. 1, the cartridge 102 is inserted through the back of the device 100. The cartridge 102 is connected to supply the scalp or hair formulation to the dispenser 112. In one embodiment, the device 100 can hold multiple cartridges, wherein each cartridge is filled with a different formulation, which can be dispensed to effect different treatments and to different regions of the scalp and hair.

In one embodiment, the cartridge 102 has a product identification tag that can convey instructions for operation of the device 100 based on the specific formulation contained in the cartridge 102. The device 100 may include a product identification tag reader capable of reading the product identification tag and processing the encoded signals into instructions for operation and control of the device based on the particular formulation. Product dentification tags, include for example, bar codes, 2-D bar codes, RFID, and the like. The product identification tag is encoded with machine readable signals that convey the device settings for the particular formulation. Different formulations may have different device settings. For example, the product identification tags can include dispenser setting from liquid to fine, medium, or coarse droplets. Product identification tags can also include the dispenser pattern formation, such as flat fan versus cone, wide versus narrow, solid versus hollow, stream versus mist. Product identification tags can also contain instructions for operating the LEDs 202, 204, 1102, 1202. Different formulations can also be used for treating different regions of the scalp and hair. Different formulations may also be used to provide different treatments to the scalp and hair.

The dispenser 112 can dispense one or more formulations through the tips 602, 702, 1100, 1200 as a fine mist or liquid or any form in-between. In one embodiment, the dispenser 112 includes a compressor, pump, or ultrasonic wave generator to generate a mist from the formulation. In the case of a pump or compressor dispenser 112, such dispenser 112 causes air or the formulation to flow at a high velocity which propels the formulation through a fine openings. In the case of a pump or compressor dispenser, a single dispenser 112 can be placed in the device 100. Then, the outlet of a compressor or pump dispenser 112 is routed through a system of conduits to each of the individual tips.

In an embodiment, the dispenser 112 is an ultrasonic wave nebulizer that generates a mist or vapor to dispense the formulation through individual tips. This has the advantage of gentle dispersion of the formulation to reduce the amount of waste and improves control of coverage. In one embodiment, the nebulizer uses an ultrasonic wave generator that is in contact with the formulation where the frequency of the ultrasonic waves is sufficient to produce the mist. An ultrasonic wave nebulizer also includes a "mesh" nebulizer that has a vibrating mesh just touching the surface of the formulation to create the mist. Either form of ultrasonic wave nebulizer can use a piezoelectric element.

In one embodiment, the ultrasonic wave generator and vibrating mesh nebulizer may both use a piezoelectric material to generate vibrations in the ultrasound frequencies. In one embodiment, the same piezoelectric material that is used in the nebulizer may also be used to drive a haptic system. A haptic system can include a massage therapy system, but, may also include any system that provides a sensory experience, such as heating and related ultrasound therapies. Nebulizers may rely on generating frequencies of over 1 MHz. A nebulizer capable of producing frequencies of over 1 MHz, may also be used to drive a haptic system to generate heat that can be used to treat the skin and scalp either alone or together with the dispensing of formulations. Some nebulizers may also rely on ultrasound frequencies less than 1 MHz. In one embodiment, the nebulizer can be used to drive a haptic system to generate frequencies in a range designed to deliver therapeutic compounds to the skin and scalp in conjunction with the dispensing of formulations. Therefore, there are advantages when the same piezoelectric material that is used in the nebulizer system is used in a haptic system.

In one embodiment, each of the tips may include a valve at the entrance to one or both chambers. The valve has an actuator that opens and closes the valve. Each valve of each tip can be actuated to open or close independently of the other valves of other tips. By opening or closing the valve at each individual tip, the formulation can be controlled to flow out only from selected tips in a controlled pattern, such as cone, flat fan, stream, multiple streams, in pulses, and the like. Further, having a valve to control dispensing from both chambers of a tip allows controlling the formulations to flow out from one or both of the chambers.

Figure 9:
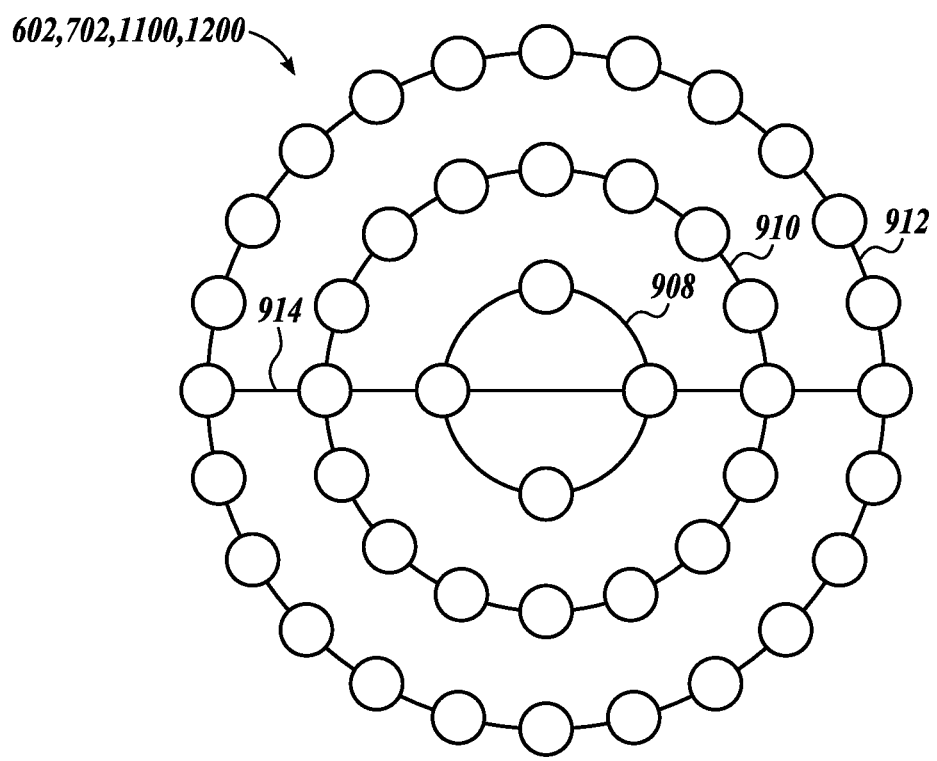
FIG. 9 is a schematic illustration showing the ends of individual tips being controlled to dispense formulation in circular and linear patterns.

FIG. 9 is a schematic illustration showing the ends of the tips 602, 702, 1100, 1200. "Ends" can be used to designate the orthogonal direction with respect to the length of the tips, and can also mean being in proximity to the orthogonal direction, such as along the length next to the orthogonal direction. In one embodiment, the tips are arranged in increasing diameter circular patterns of small 908, medium 910, and large 912 diameters. In one embodiment, only the valves of tips connected by one of the circles 908, 910, or 912 can be opened, leading to dispensing of the formulation in a small cone 908, medium cone 910, and large cone 912, to cover small, medium, and large areas of the scalp or hair. A controller is instructed to open the tips that lie in a pattern to dispense the formulation according to the pattern and closes the tips that do not lie in the pattern. The actuation of valves of individual tips is not limited to only circular patterns. In one embodiment, the valves of tips can be actuated in a linear pattern. Line 914 connects only the tips that would be opened to dispense formulation in a fan pattern, while the remaining tips that do not lie in the linear pattern would be kept closed. Any combination of individual tips can be selected to dispense formulation from only certain tips, but not others, to achieve distinct patterns.

In one embodiment, the dispenser 112 operates by depressing the switch 106. In one embodiment, the switch 106 is a momentary switch with the default position being the off position. A momentary switch only needs to be activated once, regardless of length of activation, to dispense a measured amount of formulation. Keeping a momentary switch 106 depressed longer does not dispense more formulation beyond the pre-measure amount. In another embodiment, the switch 106 is an on-off switch that starts and stops the dispenser 112 based on opening and closing the switch.

In one embodiment, the valves on tips 602, 702, 1100, and 1200 are only actuated if the individual tip that is selected for dispensing is in contact with the skin. In one embodiment, the tips 602, 702, 1100, and 1200 being made from conductive materials allows the tips to act as contact sensors. In one embodiment, one of the cylinders of each of the tips 602, 702, 1100, and 1200 can act as a positive terminal, while a second cylinder of the same or different tip acts as a negative terminal. In one embodiment, impedance can be measured between any positive terminal of a tip and any negative terminal of a tip to determine if one or more individual tips are in contact with scalp (skin). In one embodiment, impedance can be measured between any positive terminal and the scalp (via a conductive return path to handle)/Determining impedance and contact is useful if the application requires scalp contact; for instance, in a formula treatment and vacuuming system, where the scalp is being treated and the vacuum is at risk of vacuuming hair if the device is not operating directly on the scalp.

In one embodiment, the measure of impedance can also be used to calculate scalp moisture level at a specific point or over a more general region. In one embodiment, impedance can be measured from different tips to determine scalp moisture level across wider regions.

In one embodiment, a contact sensor 162 can be placed at the tip ends. In one embodiment, the contact sensor 162 includes open or short detectors or dielectric sensors. An open detector can refer to an open circuit detector for detecting a broken (open) continuity in an electrical transmission. A short detector can refer to detection of low electrical resistance. A dielectric sensor is also referred to as a capacitance detector which can detect a change in dielectric permittivity. In one embodiment, the contact sensor 162 may be a sensor that detects contact or no contact of an individual tip. In one embodiment, the contact sensor 162 may indicate the amount of contact. An example of a contact sensor that can detect an amount of contact is a piezoelectric sensor.

Figure 11:
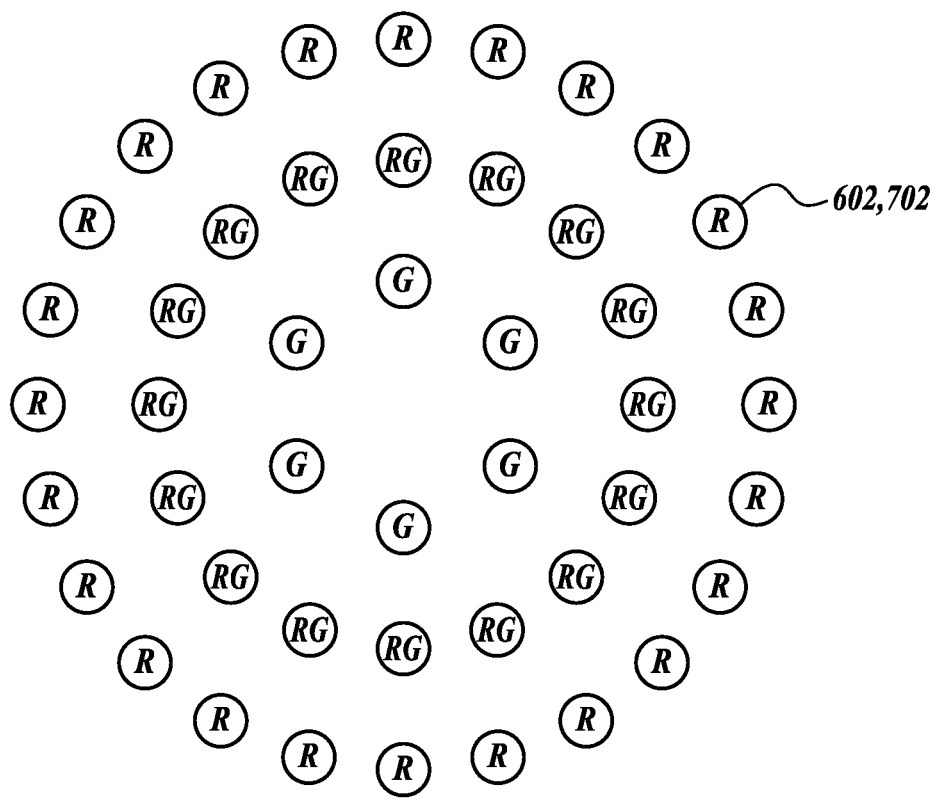
FIG. 11 is a schematic illustration showing the ends of individual tips with LEDs that emit light in the visible color spectrum being individually controlled to light up.

In one embodiment, the device 100 includes a light module 152. The light module 152 has circuitry configured to control the LEDs 202, 204, 1102, 1102 at the ends of the tips. In one embodiment, the light module 152 has circuitry configured to control which LEDs are turned on and off, the rate at which they are turned on and off, and the brightness and/or intensity of each LED at its respective wavelength. The light module 152 circuitry can be included within the controller 148 or be separate from the controller. Particularly, referring to the RGB LEDs 202, the light module 152 has circuitry configured to control the turning on and off and vary the intensity of red light, green light, and blue light emitted from each of the RGB LEDs 202. By turning on and varying the intensity of the individual red, green, and blue LEDs of the RGB LED 202, many different colors can be produced from the tips individually, where some tips can be lit to produce a certain color and other tips are lit differently FIG. 11 illustrates a view of the ends of tips 602, 702, wherein each one of the tips is fitted with an RGB LED 202 at the end. "Ends" can be used to designate the orthogonal direction with respect to the length of the tips, and can also mean being in proximity to the orthogonal direction, such as along the length next to the orthogonal direction. In this illustrated example, the light module 152 turns on the red LEDs of the outer circle of tips, turns on the red and green LEDs of the middle circle of tips, which combines to give yellow, and turns on the green LEDs of the inner circle of tips. In an embodiment, the RGB LEDs 202 at the tips can be controlled to give any color red, green, or blue, or a certain color by combining any two or more of red, green, and blue colors. By turning on and varying the intensity of each red, green, and blue LED individually, many shades of colors can be achieved at each tip. Each tip can be lit to give the same color or different tips can be lit to give different colors. Furthermore, the ability to individually control the light emitted from each tip allows creating alphanumeric characters, such as numbers and letters that can be spell out notices by lighting up only certain tips. Individual tips with RGB LEDs can be lit up in different colors up to represent different modes. Through the use of different colors or lighting specific tips, the RGB LEDs 202 can be used to display detailed device information, such as charge status, operating mode, cartridge level, or pleasing visuals by creating an RGB pixel-like display. In one embodiment, the RGB LEDs 202 operate to give the status or provide visual displays when the device 100 is in the closed position (FIG. 3). In the closed position, the light emitted by the RGB LEDs is visible through a diffuser material 136 which can scatter the light to fill in the gaps between tips to provide a pleasing visual effect as well as provide useful device status information.

In one embodiment, the device 100 includes a vacuum system 114 having a vacuum generating motor and collector 116. In one embodiment, a motor can be a variable speed motor. The vacuum motor 114 is connected to impeller vanes that cause a stream of air to enter through one of the cylinders of the tips 602, 702, 1100, and 1200. The motor induces a stream of air to enter through the tip openings. The stream of air can carry the used formulation along with any debris and oils washed out of the hair by the formulation, which then gets captured by a collector 116, and the air is expelled out of the device 100. In one embodiment, the collector 116 includes an annular vent placed at the back of the device 100. The vent allows the stream of air to exit the device 100, while the used and debris become trapped in the collector 116.

In one embodiment, the vacuum motor 114 is operated by the multi-positional, multi-functional, selector switch 110. A selector switch 110 can be a slide switch or a dial switch with more than two positions, or a push button switch with more than two positions, for example. In one embodiment, a vacuum selector switch 110 includes settings for off and more than one vacuum speed setting, such as high and low. In one embodiment, the vacuum switch 110 is placed on the back side of lower part of the handle 104 to allow operation with the thumb, for example. The vacuum switch 110 can be isolated for uninterrupted vacuum. The selector switch 110 remains in the selected position until moved to another position. In one embodiment, a momentary switch can replace the selector switch, wherein the default position of the momentary switch is the off position, and the momentary switch has to be depressed to start the vacuum motor. In one embodiment, the device 100 includes both a vacuum selector switch and momentary switch, wherein the momentary switch is used to operate the vacuum motor when depressed, and at the speed setting on the selector switch.

In one embodiment, the device 100 includes a controller 148. In one embodiment, the controller 148 is a digital device. The controller 148 may include one or more hardware circuits connected on a printed circuit board, or all of circuits may exist on a single chip. The controller 148 may include at least a microprocessor core and a memory. The hardware can be designed for use in small hand operated devices. The microprocessor may be implemented as multiple processors cooperatively working in parallel and series to perform instructions according to pre-programmed logic.

Instructions to control the dispenser 112, vacuum 114, light module 152 can be stored in the controller memory. A memory is any type of computer-readable medium or computer storage device that can be accessed and used by one or more microprocessors to carry out the instructions. Instructions may be stored in a high-speed memory such as a EEPROM, Flash memory, RAM, or other programmable non-volatile memory.

The controller 148 communicates with the dispenser 112, light module 152, vacuum 114 to make decisions and control the output from the device 100 based on inputs received form the tips 602, 702, 1100, 1200 themselves, the LEDs 202, 204, 1102, 1202, and/or contact sensor 162.

In one embodiment, the controller 148 is configured to turn on and off and vary the intensity of the light from individual LEDs that emit light in the visible color spectrum so that the color of light emitted from each individual tip can be different. In one embodiment, the controller 148 is configured to turn on and off and vary the intensity of the light from individual LEDs of the RGB LEDs 202 so that the color of light emitted from each individual tip can be different.

In one embodiment, the controller 148 can also interpret the information provided on cartridges 102 to give instructions to the dispenser 112 that are specific to the formulation. The controller 148 can control to open and close all of the tips 602, 702, 1100, and 1200 to allow formulation to be dispensed through individually selected tips in a pattern.

In one embodiment, the controller 148 has circuitry to determine the impedance between terminals of any one or more tips to determine which tips are in contact with the skin and which tips are not in contact with the skin. The controller 148 can then open those valves on the tips that are in contact and close the valves that are not in contact, and give permission to the dispenser to proceed with dispensing formulation through the tips in contact with skin.

In one embodiment, the controller 148, the controller 148 has circuitry to determine the impedance between terminals of any one or more tips to determine which tips are in contact with or in close proximity to the skin and which tips are not in contact with the skin. The controller 148 can then turn on only those LEDs of the tips that are in contact with or in proximity to the skin.

In one embodiment, the controller 148 uses the impedance to determine whether the tips are in contact with the scalp. In one embodiment, the controller 148 can turn off the vacuum 114 or not allow the vacuum to be turned on when it is determined that one or more tips are not in contact with the scalp.

In one embodiment, the controller 148 can use a measure of the impedance to determine the moisture of one or more regions on the scalp.

In one embodiment, the controller 148 receives signals from the contact sensor 162 to determine whether or not tips are in contact with the skin.

In one embodiment, the controller 148 has circuitry to control the opening of valves of only those tips that will produce a selected spray pattern.

In one embodiment, the controller 148 has circuitry to control the amount of formulation that is dispensed by the dispenser.

In one embodiment, the controller 148 is configured to provide power to any one or more of the tips.

In one embodiment, the controller 148 has circuitry to turn on the LEDs 1102 and 1202 based on pre-determined instructions. For example, some formulations may call for applying light in a certain wavelength. The controller 148 may be used to turn on and off the LEDs 1102 and 1202 to provide a light therapy treatment. The controller 148 has instructions for the wavelength that is to be used and power to be applied for the light therapy, and then power the appropriate wavelength LED.

In one embodiment, the controller 148 has circuitry to control the amount of formulation that is dispensed by the dispenser 112. For example, the controller 148 can turn on a pump or compressor for a predetermined amount of time that correlates to a specific amount of formulation. In one embodiment, the dispenser 112 uses a positive displacement pump, therefore, the volume displaced for each rotation of the pump can be measured with an encoder. When the rotations of the pump equal the volume of formulation to be dispensed, the controller 148 can turn off the pump.

In one embodiment, the controller 148 has circuitry configured to control the dispenser 112 to dispense a measured volume of formulation through one or more of the tips only when the controller 148 senses that the tips are in contact with the scalp.

In one embodiment, the controller 148 has circuitry configured to turn on and off LEDs of a certain wavelength for applying a therapeutic light treatment or be used to cure formulations.

In one embodiment, the controller 148 has circuitry configured to control the vibration of selected individual tips.

In one embodiment, the controller 148 has circuitry configured to control the dispensing of a measure amount of formulation through selected individual tips only upon detecting the tips are in contact with the scalp/skin.

Use of the device 100 is instinctive, the overall shape of the device 100 is familiar to users from other hair appliances, such as a hair dryer, leading to simple intuitive use of the device 100. The device 100 can improve on current use of aerosol dry shampoos. The device 100 contrasts with an aerosol spray can that sprays more than is needed and produces a large cloud that covers an area well outside the user's head. Furthermore, the device 100 has tips that allow added functionality.

While illustrative embodiments have been illustrated and described, it will be appreciated that various changes can be made therein without departing from the spirit and scope of the invention.

The embodiments of the invention in which an exclusive property or privilege is claimed are defined as follows:

1. A hair and scalp treatment device, comprising:
   a dispenser connected to a cartridge, wherein the cartridge comprises a formulation;
   a plurality of tips on the device, wherein the plurality of tips include at least one terminal to measure impedance, and wherein the tips have at least one opening to dispense the formulation and at least one LED that emits light in the visible color spectrum, wherein the at least one LED is located at the end of the tips;
   a controller configured to individually turn on and off the LEDs from the plurality of tips and to dispense the formulation from the plurality of the tips having an impedance measurement indicating contact with the skin; and a handle and a section with a brush head comprising the plurality of tips, wherein the end of the handle includes a diffuser material visible on the exterior of the handle.

2. The device of claim 1, wherein the at least one LED is an RGB LED.

3. The device of claim 1, wherein the tips include conductive wiring to power the LEDs.

4. The device of claim 1, wherein the tips further include a UV or IR LED or both UV and IR LEDs at the end of the tips.

5. The device of claim 1, wherein the at least one LED is sealed in a light transparent cap.

6. The device of claim 1, wherein the section with the brush head pivots to recede within the handle.

7. The device of claim 1, wherein the LEDs display device status through color.

8. The device of claim 7, wherein the status is one of at least battery charge status, operating mode, or cartridge fill level.

9. The device of claim 1, wherein the at least one LED is an RGB LED comprising a red LED, a green LED, and a blue LED, and wherein the controller controls the color of the tips.

10. The device of claim 1, wherein the tips include conductive wiring shaped into coils.

11. A hair and scalp treatment device, comprising:
a dispenser connected to a cartridge, wherein the cartridge comprises a formulation;
a plurality of tips on the device, wherein the tips have at least one opening to dispense the formulation and at least one LED that emits light in the visible color spectrum, wherein the at least one LED is located at the end of the tips;
a controller configured to individually turn on and off the LEDs from the plurality of tips;
a handle and a section with a brush head comprising the plurality of tips, wherein the section with the brush head pivots on the handle;
wherein the LEDs are positioned next to a diffuser material upon pivoting the handle to a closed position.

12. The device of claim 11, wherein the diffuser material scatters the light emitted by the LEDs.

* * * * *